United States Patent
Rodrigues Quintas et al.

(10) Patent No.: US 9,198,602 B2
(45) Date of Patent: Dec. 1, 2015

(54) DEVICE FOR MEASURING SKINFOLD THICKNESS

(75) Inventors: Manuel Rodrigues Quintas, Oporto (PT); Carlos Manuel Sousa Moreira Da Silva, Oporto (PT); Tiago Faustino Andrade, Oporto (PT); Maria Teresa Braga Valente De Almeida Restivo, Oporto (PT); Maria de Fátima De Castro Chousal, Oporto (PT); Teresa Maria De Serpa Pinto Freitas Do Amaral, Oporto (PT)

(73) Assignee: UNIVERSIDADE DO PORTO, Oporto (PT)

( * ) Notice: Subject to any disclaimer, the term of this patent is extended or adjusted under 35 U.S.C. 154(b) by 367 days.

(21) Appl. No.: 13/807,658

(22) PCT Filed: Dec. 9, 2010

(86) PCT No.: PCT/IB2010/055701
§ 371 (c)(1),
(2), (4) Date: Jan. 31, 2013

(87) PCT Pub. No.: WO2012/001467
PCT Pub. Date: Jan. 5, 2012

(65) Prior Publication Data
US 2013/0123668 A1 May 16, 2013

(30) Foreign Application Priority Data
Jul. 2, 2010 (PT) .................................. 105187

(51) Int. Cl.
*A61B 5/107* (2006.01)
*G01B 3/00* (2006.01)
(Continued)

(52) U.S. Cl.
CPC ............. *A61B 5/1075* (2013.01); *A61B 5/1072* (2013.01); *A61B 5/4872* (2013.01); *G01B 3/008* (2013.01); *G01B 3/16* (2013.01); *A61B 5/0002* (2013.01)

(58) Field of Classification Search
CPC .. A61B 5/1072; A61B 5/1075; A61B 5/4872; A61B 5/0002
USPC .................................. 600/587; 33/512
See application file for complete search history.

(56) References Cited

U.S. PATENT DOCUMENTS 3,008,239 A 11/1961 Lange
4,127,112 A * 11/1978 Sherlock et al. .............. 600/587
(Continued)

FOREIGN PATENT DOCUMENTS

CH           243 735 A      7/1946
WO      WO 93/17297 A1     9/1993

OTHER PUBLICATIONS

International Search Report, mailed Jul. 22, 2011 in connection with PCT International Application No. PCT/IB2010/055701, filed Dec. 9, 2010.

*Primary Examiner* — Michael C Stout
(74) *Attorney, Agent, or Firm* — John P. White; Cooper & Dunham LLP

(57) ABSTRACT

The object of the present invention is a device for measuring skinfold thickness digitally instrumented for reading the thickness of skin folds and possessing wireless data communication capability with a remote station (for example, a personal computer) in which is installed a software application integrating a database.

The developed device utilizes working principles distinct from those available in the market, in particular uses a constant force actuator (11) integrated in the device handle (12A), whose primary function is to impose a constant contact pressure between the end tip faces (1A and 1B) and the skinfold under measurement. Another characteristic is related to the increase of the opening limit of the end tips (1A and 1B) by using a large center distance for the jaws pivot axes, jointly with a cam for compensating the change in the force arm length, the constant force actuator and the orientation mechanism of the clamping faces of the end tips, whereby the application of a constant pressure throughout the whole measuring range is accomplished.

11 Claims, 13 Drawing Sheets

(51) Int. Cl.
*G01B 3/16* (2006.01)
*A61B 5/00* (2006.01)

(56) References Cited

U.S. PATENT DOCUMENTS

| 4,201,226 | A | * | 5/1980 | Phillips | 600/587 |
| 4,315,372 | A | * | 2/1982 | Kinkead | 33/798 |
| 5,156,161 | A | * | 10/1992 | Lollar | 600/587 |
| 5,430,954 | A | * | 7/1995 | Best et al. | 33/793 |
| 6,301,799 | B1 | * | 10/2001 | Ho | 33/807 |
| 2006/0162178 | A1 | * | 7/2006 | Freidin | 33/784 |
| 2010/0256519 | A1 | * | 10/2010 | Vidal et al. | 600/562 |

* cited by examiner

DEVICE FOR MEASURING SKINFOLD THICKNESS

CROSS-REFERENCE TO RELATED APPLICATIONS

This application is a §371 national stage of PCT International Application No. PCT/IB2010/055701, filed Dec. 9, 2010, claiming priority of Portuguese Patent Application No. 105187, filed Jul. 2, 2010, the contents of each of which are hereby incorporated by reference in their entirety.

The object of the present invention is a device for measuring skinfold thickness digitally instrumented for reading the said thickness and presenting the measured values in a display that can have tactile capabilities for interaction with the operator.

The said device can also integrate wireless data communication capabilities with a remote station (for example, a personal computer), where resides a software application integrating a database.

BACKGROUND OF THE INVENTION

The investigation of the state of the art disclosed three patent documents considered as the closest "prior art".

Devices for measuring skinfold thickness are known in the state of the art. Such is the case of the device described in the U.S. Pat. No. 3,008,239 referring to an apparatus for measuring skinfold thickness with jaws prepared for applying constant force. However this patent does not describe the mechanism generating constant force, which is one of the aims of the present invention and which permits to multiply the spring force.

The U.S. Pat. No. 4,315,372 also describes a device for measuring skinfold thickness with C-shaped jaws and also incorporating a spring in a central position that permits the application of constant force. As in the previous document this patent document does not describe the mechanism for the constant force actuator that is one of the aims of the present invention.

Finally, the document WO9317297 refers to a device possessing two jaws and a sensor for reading the jaws displacement and converting this displacement into the skinfold thickness measurement. This patent does not describe the use of a mechanism generating a constant force.

SUMMARY

It is the objective of the present invention to describe a device for measuring skinfold thickness which comprises:
- one device housing (12B), preferably of closed cylindrical shape, with a device handle (12A);
- one structure with two jaws (3A and 3B) with hinged and mechanically oriented end tips (1A and 1B), and one lever (16);
- one constant force actuator mechanism (11);
- one cam (4) with a profile that compensates the variation of the force arm length in the jaws (3A and 3B) and which provides the transmission of the force generated by the said constant force actuator (11).

In a preferential embodiment of the device for measuring skinfold thickness in the present invention, the constant force actuator (11) comprises a crescent shaped saddle (11A) which supports at least one constant force elastic element (11D), two drums (11C1) and (11C2), two bearings (11B1) and (11B2), two rotation axes (11E1) and (11E2).

In other embodiment even more preferential the device for measuring skinfold thickness has a large centre distance of the jaws rotation axes and comprises one cam for compensation of variations in the jaws force arm length, one constant force actuator (11) and one orientation mechanism for the end tips (1A and 1B), permitting measurement of skinfold thickness of at least 110 mm, with application of a constant pressure to the skin folds.

In other preferential embodiment the device for measuring skinfold thickness comprises a mechanism for transmission of movement to the end tips based on the following systems: one parallelogram shaped mechanism with bars in tension and/or compression, one inextensible cable mechanism under tension by elastic element action and one flexible element mechanism confined in its housing.

In an embodiment even more preferential of the device for measuring skinfold thickness object of the present invention, the elastic element of the constant force actuator (11D) is based on a constant force spring.

In other embodiment even more preferential the device for measuring skinfold thickness incorporates a mechanism for multiplying the jaws angular displacement that is able to increase the resolution of the measurement of the distance between the faces of the end tips (1A and 1B).

In other embodiment even more preferential of the device for measuring skinfold thickness the device housing (12A and 12B) accommodates all the mechanical elements for the transmission of the force of the constant force actuator (11) to the jaws (3A and 3B), the sensing elements (10A and 10B) and the electronic system (20).

In other embodiment even more preferential of the device for measuring skinfold thickness, it has hinged and oriented end tips (1A and 1B) preferentially with contact surfaces that are kept parallel by means of a mechanism actuated by the jaws (3A and 3B) opening/closing, the said end tips being thereby able to apply a constant pressure to the skinfold under measurement.

In other preferential embodiment the device for measuring skinfold thickness also comprises one electronic system integrating one rechargeable power supply system, one signal conditioning system, one dedicated microcontroller and one wireless communication system.

In other embodiment even more preferential the device for measuring skinfold thickness also comprises one window (21) which permits wireless communication with a remote station and the visualization of light indicators for user information.

In other embodiment even more preferential the device for measuring skinfold thickness comprises one on/off switch, one display and one navigation system all located in the device symmetry plan, in order to make the handling of the said device independent of the dominant hand of the operator.

BRIEF DESCRIPTION OF THE DRAWINGS

For better understanding of the invention figures are included in annex, which represent preferential embodiments of the invention but are not intended to limit the object of the present invention.

6A and 6B—Axis of rotation of the jaw A and B, respectively;
7—Inextensible cable;
8—On/off switch;
9—Device for remote interaction;
10A—Encoded sensing element;
10B—Reading sensing element;
11—Constant force actuator;
12A—Device handle;
12B—Device cylindrical body;
13—Power supply;
14—Power charging jack;
15—Measurement reset button;
16—Lever;
17—Trigger button for the time interval of the measurement protocol;
18—Spiral spring of the encoded sensing element;
19—Mechanical element for increasing the measurement resolution;
20—Electronic system;
21—Window for communication and visualization of the light indicators;
22—Device lateral faces;
23—Light indicator of the device power supply status;
24—Light indicator of the on/off status of the electronic system (20);
25—Light indicator of the on/off status of the device connection to the remote station.

32A and 32B—Floating hinge of the inextensible cable/secondary bar (35A and 35B) in the coupling element (28A and 28B), respectively;

33A and 33B—Floating hinge of the inextensible cable/secondary bar (35A and 35B) in the end tip (1A and 1B), respectively;

34A and 34B—Inextensible cable/primary parallelogram bar A and B, respectively;

35A and 35B—Inextensible cable/secondary parallelogram bar A and B, respectively;

36A and 36B—Elastic element located in jaw (3A and 3B), respectively.

Figure 6:
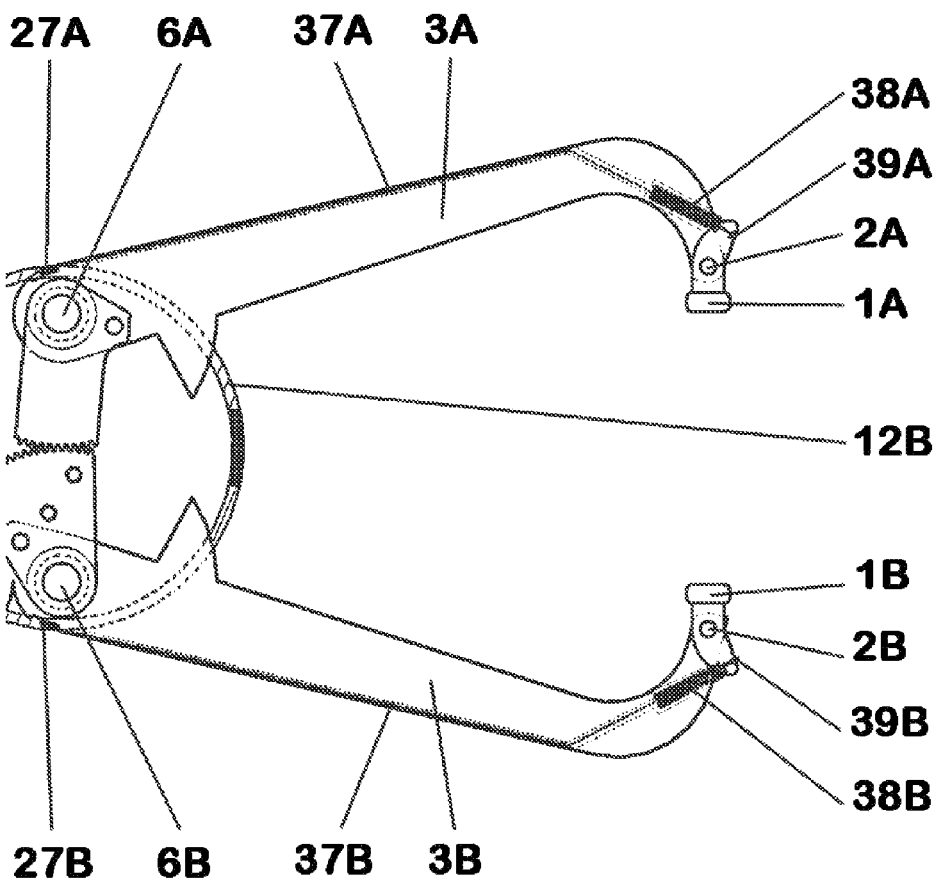

FIG. 6: Representation of a transmission mechanism of angular movement to the end tips, for maintaining the parallelism of their clamping faces, using a configuration based on an inextensible cable in tension by the action of elastic element, with the following components:

1A and 1B—End tip A and B, respectively;
2A and 2B—Axis of rotation of the end tip A and B, respectively;
3A and 3B—Jaw A and B, respectively;
6A and 6B—Axis of rotation of the jaw A and B, respectively;
12B—Device cylindrical body;
27A and 27B—Anchoring point, on the cylindrical body (12B), of the inextensible cable (37A and 37B), respectively;
37A and 37B—Inextensible cable located in jaw (3A and 3B), respectively;
38A and 38B—Elastic element located in jaw (3A and 3B), respectively;
39A and 39B—Anchoring point of the inextensible cable (37A and 37B) on the end tip (1A and 1B), respectively.

Figure 7:
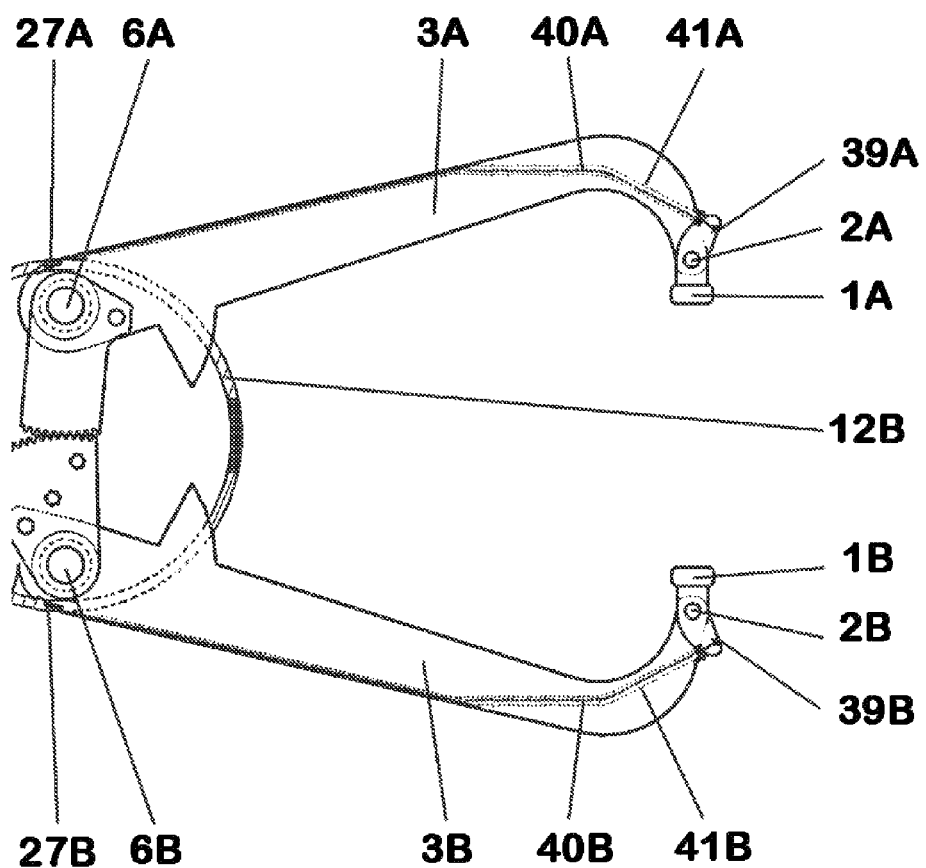

FIG. 7: Representation of a transmission mechanism of angular movement to the end tips, for maintaining the parallelism of their clamping faces, using a configuration based on a flexible element in compression confined in its housing, with the following components:

1A and 1B—End tip A and B, respectively;
2A and 2B—Axis of rotation of the end tip A and B, respectively;
3A and 3B—Jaw A and B, respectively;
6A and 6B—Axis of rotation of the jaw A and B, respectively;
12B—Device cylindrical body;
27A and 27B—Anchoring point, on the cylindrical body (12B), of the flexible element (40A and 40B), respectively;
39A and 39B—Anchoring point of the flexible element (40A and 40B) on the end tip (1A and 1B), respectively;
40A and 40B—Flexible element located in jaw (3A and 3B), respectively;
41A and 41B—Flexible element housing (40A and 40B).

Figure 8:
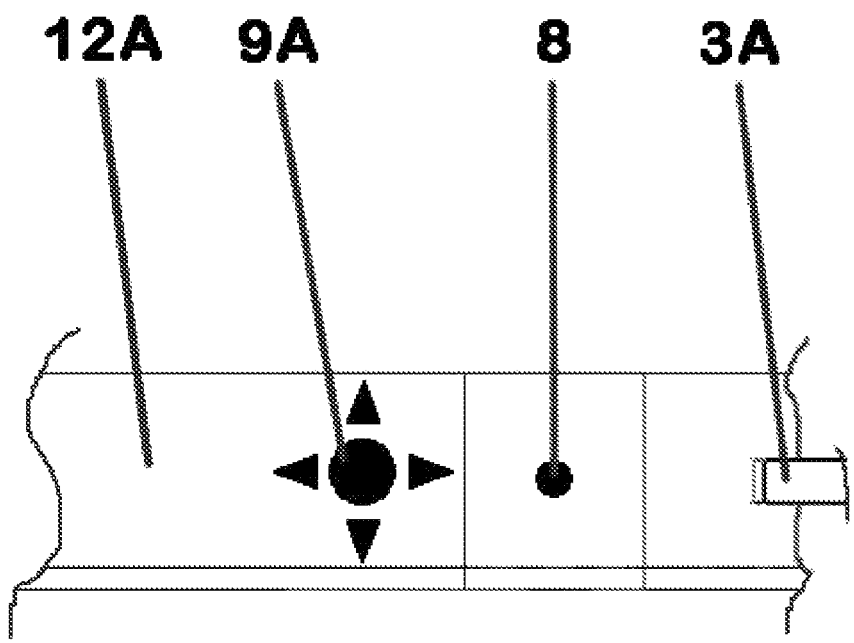

FIG. 8: Representation of a navigation system for interaction with the graphical interface of the computer application, using a joystick-type button, with the following components:

3A—Jaw A;
8—On/off switch;
9A—Joystick-type navigation button;
12A—Device handle.

Figure 9:
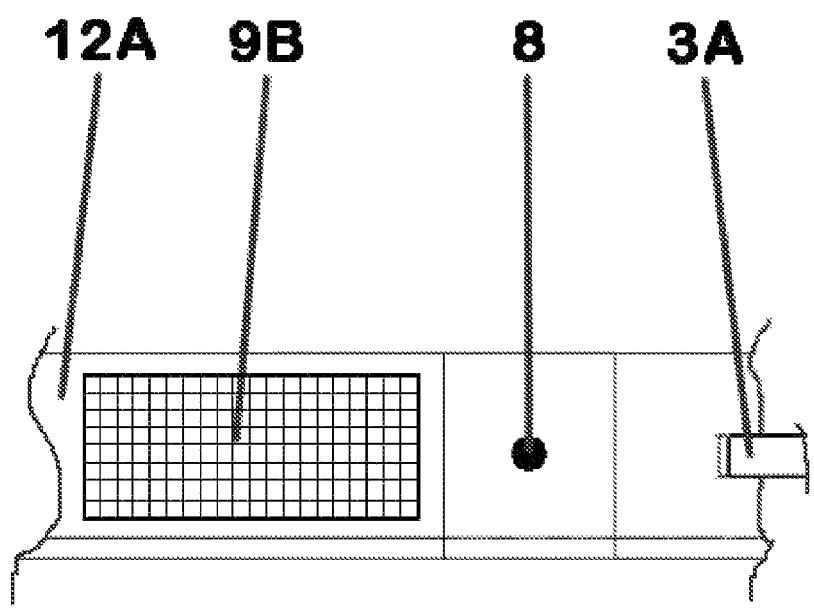

FIG. 9: Representation of a navigation system allowing interaction with the graphical interface of the computer application, using a touchscreen, with the following components:

3A—Jaw A;
8—On/off switch;
9B—Touchscreen;
12A—Device handle.

Figure 10:
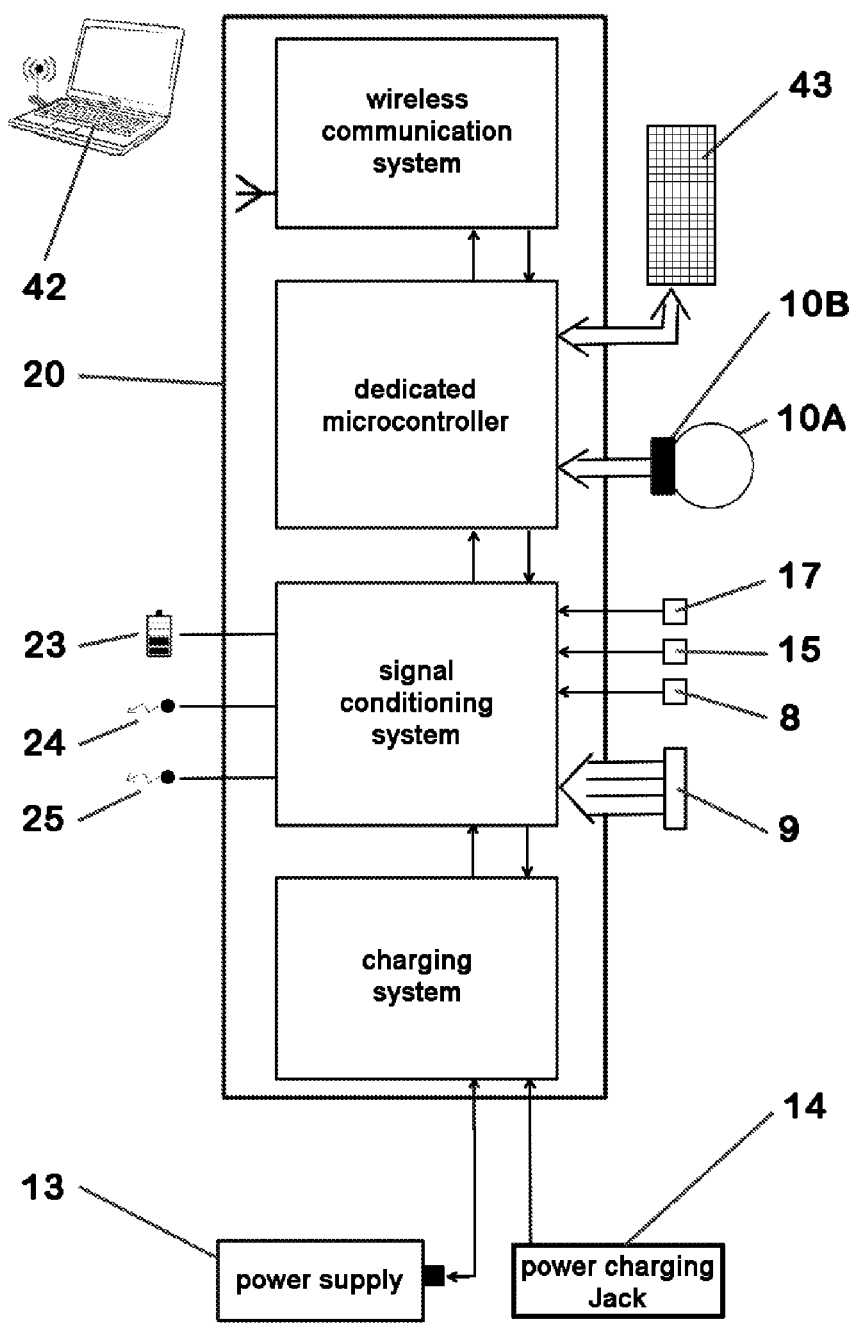

FIG. 10: representation of an electronic system, with the following components:

8—On/off switch;
9—Device for remote interaction;
10A—Encoded sensing element;
10B—Reading sensing element;
13—Power supply;
14—Power charging jack;
15—Measurement reset button;
17—Trigger button for the time interval of the measurement protocol;
20—Electronic system;
23—Light indicator of the device power supply status;
24—Light indicator for the on/off status of the electronic system (20);
25—Light indicator of the on/off status of the device connection to the remote station;
42—Remote station;
43—Device display.

Figure 11:
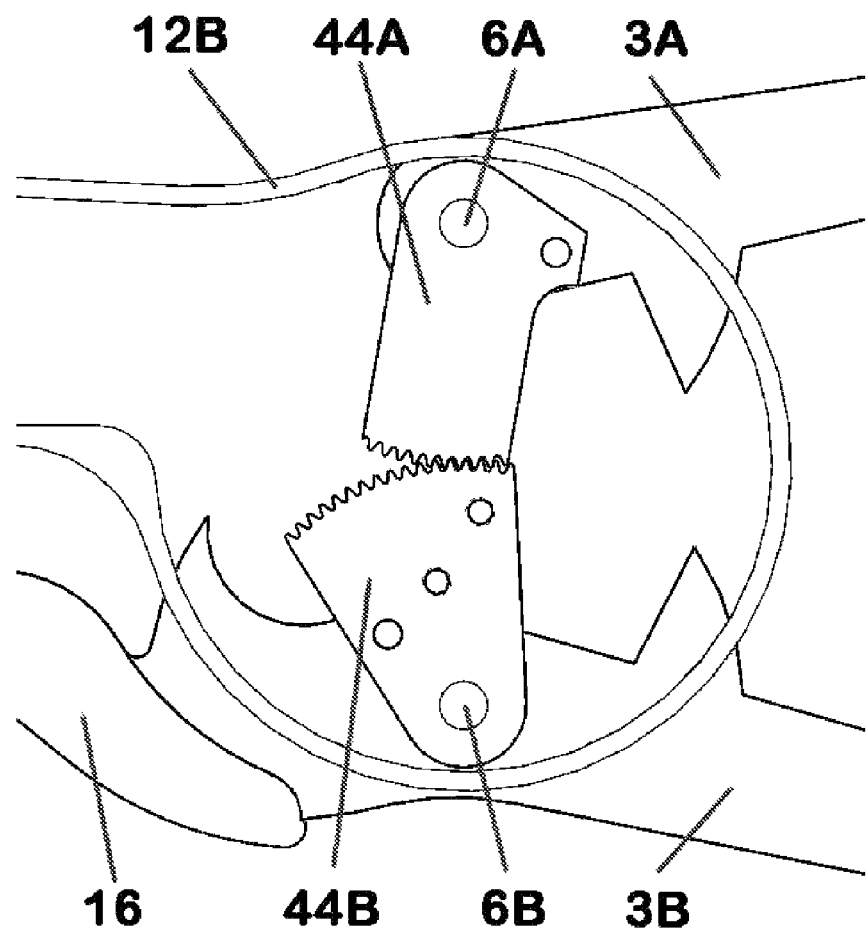

FIG. 11: Representation of a transmission system by toothed sectors which provides simultaneous opening of the jaws:

3A and 3B—Jaw A and B, respectively;
6A and 6B—Axis of rotation of the jaw A and B, respectively;
12B—Device cylindrical body;
16—Lever;
44A and 44B—Toothed sectors A and B, respectively.

Figure 12:
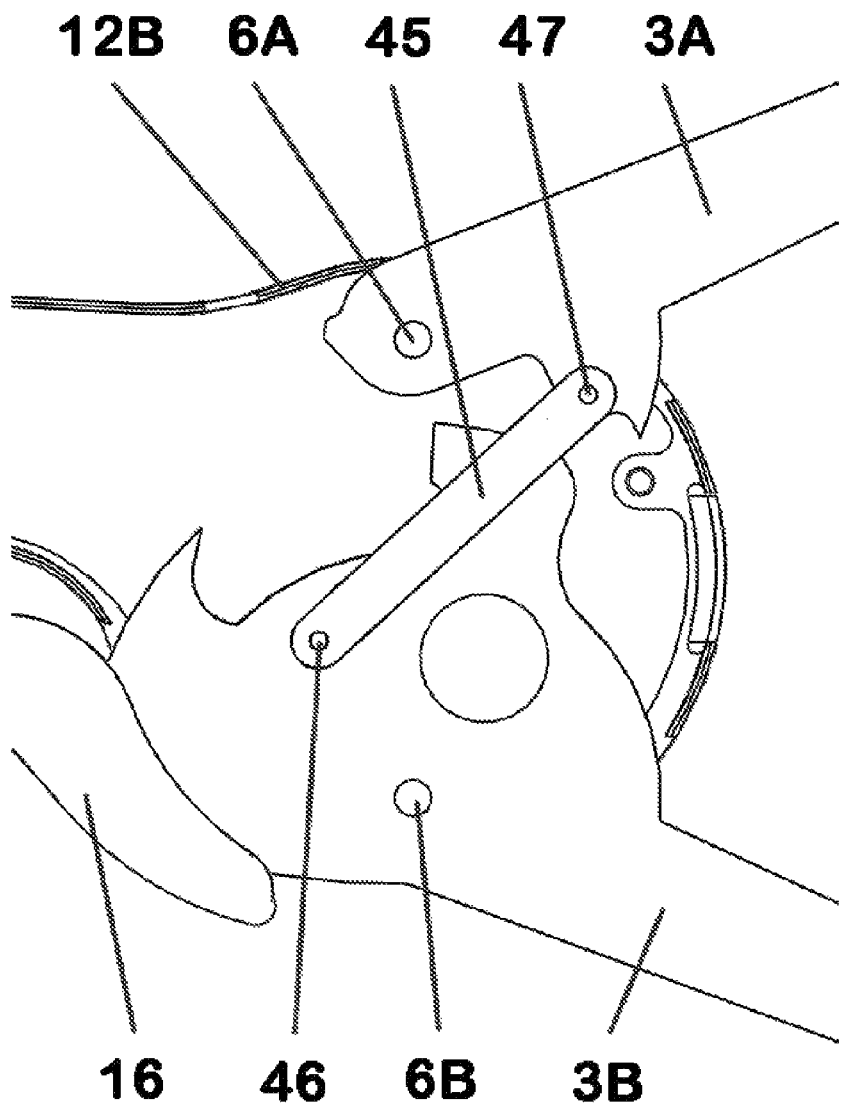

FIG. 12: Representation of a transmission system by a four-bar hinged joint mechanism that allows the simultaneous opening of the jaws:

3A and 3B—Jaw A and B, respectively;
6A and 6B—Axis of rotation of the jaw A and B, respectively;
12B—Device cylindrical body;
16—Lever;
45—Transmission bar;
46—Axis of rotation of the transmission bar (45);
47—Axis of rotation of the transmission bar (45);

DETAILED DESCRIPTION OF THE INVENTION

The developed apparatus uses working principles of a device for measuring skinfold thickness, integrating some additional elements for improving its accuracy and measuring range. It is a device for measuring skinfold thickness comprising one closed housing with a cylindrical part (12B) and a handle extension (12A), one structure with two jaws (3A and 3B) with hinged end tips (1A and 1B) and a lever (16).

The device housing (12A and 12B) includes all the mechanical elements of force transmission from the constant force actuator (11) to the jaws (3A and 3B), the sensing element (10A and 10B), a power supply (13) as for example a battery, its power charging jack (14) and the electronic system (20).

The cylindrical housing (12B) has a window (21) which permits a preferential embodiment for wireless communication with a remote station and the visualization of three light indicators which inform the user about the device on/off state, the on/off state of the communication with the remote station and the charge level of the power supply.

The jaws (3A and 3B) have rotation axes (6A and 6B) and extension shields inside the cylindrical housing (12B). The jaws are manipulated using the handle (12A) and the lever (16), jaw closure being controlled by one transmission chain connected at the other end to the constant force actuator (11). The constant force actuator (11) installed in the device housing handle (12A), has the main function of imposing a constant pressure on the contact faces of the end tips (1A and 1B) with the skinfold under measurement. Additionally it ensures the return movement of the jaws (3A and 3B) during closure, while also eliminating mechanical backlash along the transmission chain.

The constant force actuator (11) applies the force to the jaw (3B) by means, for example, of one inextensible cable (7) in contact with one cam (4), attached to the jaw (3B). Both jaws (3A and 3B) are interconnected by mechanical elements (5A and 5B) that accomplish their simultaneous opening.

The increase of the maximum opening distance between end tips (1A and 1B) can be achieved by enlarging the length of the jaws (3A and 3B). This consideration could be explored for this and other devices in the market. Such solution has the inconvenient of implying an increase in structural robustness, size and weight and in addition it also requires a constant force actuator of higher intensity, which demands higher user hand grip strength.

The increase of the maximum opening distance between end tips (1A and 1B) can also be achieved by providing the jaws (3A and 3B) with a larger angular opening. That is possible in this device, because it incorporates a rotating end tip (1A and 1B) mechanism which ensures the parallelism between their contact faces. Moreover the geometry of the jaws (3A and 3B) hinges minimizes the movement for accommodation of the position of the end tips (1A and 1B) by means of a large centre distance of the jaws (3A and 3B) hinges. Due to this the variation of the length of the force arm is minimized and the maximum value of the said length occurs at an intermediate point between the maximum aperture and total closure of the jaws (3A and 3B). The inclusion of the cam (4) whose profile compensates for variations in the length of the arm of the skinfold reaction force to the jaws (3A and 3B), guarantees the application of a constant force by the clamping surface of the end tips (1A and 1B) to the skinfold under measurement. With the complete stroke of the lever (16) it is possible to perform a skinfold thickness measurement of 110 mm, or higher.

This value is considerably higher than that achieved by devices available in the market whose maximum skinfold thickness measurement does not usually exceed 80 mm.

The end tips (1A and 1B) are hinged at the rotation axes (2A and 2B) in the extremities of the jaws (3A and 3B), respectively, keeping their clamping surfaces parallel to each other. The said parallelism is achieved by a movement transmission mechanism, it is independent of the opening angle of the jaws (3A and 3B) and it provides a constant uniform pressure on the whole contact area between the end tip clamping surfaces and the skinfold. In contrast to this, skinfold callipers available in the market either have end tips rigidly linked to the jaws or they do not have any parallelism control mechanism. When the end tips are rigidly linked to the jaws, they will not remain parallel to each other, and so the pressure applied to the skinfold is not uniform.

End tips with free rotation and without any mechanism for enforcing parallelism are not able to correctly control the positioning of the clamping surfaces of the end tips. Consequently they do not comply with the established protocol that prescribes a uniformly distributed pressure of $10 \, gf/mm^2$. The movement transmission mechanism for keeping the said parallelism is based on the following systems: one parallelogram shaped mechanism with bars in tension and/or compression; one inextensible cable mechanism kept under tension by the action of an elastic element and one flexible element mechanism confined in its housing.

The measurement of the distance between the clamping surface of the end tips (1A) and (1B) is performed by a sensing element (10A and 10B) integrated in the transmission chain between the constant force actuator (11) and the jaws (3A and 3B). The actuation of the sensing element (10A and 10B) is achieved through a displacement multiplication mechanism consisting in the elements (5B) and (19), which increases the resolution of the measurement of the distance between the end tip faces, for any given resolution of the encoder (10A and 10B). The backlash of the said multiplication mechanism (5B and 19) is eliminated by a spiral spring (18).

In the lever (16), connected to the driving jaw (3B), and positioned at the operator index finger level, is located the button (17) for triggering the time interval according to the protocol for the skinfold clamping procedure and another button (15) is located, for example, at the lever (16) tail end for resetting the measurement to the zero value. In the concavity between the cylindrical housing (12B) and the handle (12A) there is the device on/off button (8) and a navigation system (9) which permits remote interaction with the graphical interface of the software application. The said system is based on a navigation button (9) or a touchscreen (9B). These four command elements are in the device symmetry plane, which, in conjunction with the global device configuration, makes its handling independent of the dominant hand of the operator. In a solution for autonomous use of the device it is necessary to have a display (43) for data visualization, which may have navigation functionality if it is of tactile type (9B).

The constant force actuator (11) is based on an elastic element of constant force (11D). The said actuator multiplies the force of the elastic element of constant force (11D) by use of the said element with both ends winded on drums (11C1) and (11C2), supported by bearings (11B1) and (11B2) whose internal races are linked to the rotation axes (11E1) and (11E2), respectively. The force is conveyed to the transmission chain by a crescent shaped saddle (11A) on which the constant force elastic element (11D) rests.

The extremity of the handle (12A) houses the power supply (13) with the respective power charging jack (14).

The electronic system (20) in its distinct configurations can be composed by one power supply charging system, one signal conditioning system, one dedicated microcontroller, one display for data presentation (43) and one wireless communication system. It is responsible for the management of the whole device: it receives the operator commands through the buttons (8), (15), (17) and either from the navigation button (9A) or the touchscreen (9B), power supply level information, wireless communication data and sensing element data (10B). In accordance it controls the information supplied to the operator through the light indicators (23), (24) and (25), through the display (43) for data presentation and it is responsible for establishing the communication with the software application residing in the remote station.

The information conveyed by the navigation button (9A) or by the touchscreen (9B) can be transmitted to the remote communication station to remotely operate the graphical interface of the software application. This functionality can be seen as complementary to the use of input devices directly connected to the remote communication station, such as: keyboard, mouse and tactile screen. This is intended to expedite the measurement procedures, reducing the time waste resulting from the recurring access to the peripherals of the remote communication station for triggering the computer application commands.

The device ergonomic configuration offers considerable free lateral areas (22) on the jaws (3A and 3B), on the cylindrical housing (12B) and on the handle (12A), which are appropriate for displaying advertising elements.

Working Principle of the Device

By pressing button (8) the electronic system (20) is activated and this state is signalled by the light indicator (24). The electronic system (20) presents data for interaction with the operator through the display device and can establish contact through its wireless communication system with the remote station, which will be signalled by the flashing of the light indicator (25). The battery charge level can be visualized through the indicator (23). Insufficient charge level is reported to the computational application.

For recharging the device battery a compatible external power supply system is simply plugged to the charging jack (14). The battery charge level evolution is monitored by the evolution of the light indicator (23).

By acting upon the button (15) the zero thickness value is set.

When the operator moves the lever (16) towards the handle (12A) the button (17) remains pressed during the opening of the jaw (3B) which rotates about the axis (6B). This movement is transmitted to the mechanical part (5B) which in turn causes the simultaneous opening of the jaw (3A) that rotates around the axis (6A), while also pulling the inextensible cable (7) wound on the cam (4) which leads to a larger deflection of the constant force actuator (11). The said actuator, through the crescent shaped saddle (11A), transmits a constant opposing force to the kinematic chain. The movement of the mechanical part (5B) also leads to the actuation of the sensing element by means of a multiplication mechanism (5B and 19).

The release of the force on the lever (16) permits the adjustment of the clamping surface of the end tips (1A and 1B) to the skinfold under measurement. The pressure exerted by the tips on the skinfold comes exclusively from the constant force actuator (11), transmitted by the kinematic chain. At completion of the force release on the lever (16) and with the skinfold under the pressure of the end tips (1A and 1B), the start of the time interval defined in the protocol is triggered by releasing the pressure on button (17).

In the course of the movement of the jaws (3A and 3B), the contact surfaces of the end tips (1A and 1B) to the skinfold remain parallel to each other through the action of a parallel displacement mechanism of the end tips (1A and 1B).

The skinfold thickness is measured by the distance between the contact surface of the end tips (1A and 1B), this information being transmitted to the encoded sensing element (10A) through the kinematic chain (1B, 3B, 5B and 19). The sensing reading element (10B) transmits the reading information to the dedicated microcontroller. After being processed by the dedicated microcontroller, all the information concerning the measurement is transmitted by the display (43). This information can be transmitted by wireless communication to the computer application in the remote station. The interaction with the computer application can be made using the navigation button (9A) or the touchscreen (9B). The command conveyed by the release of button (17) for starting the protocol time interval is processed by the dedicated microcontroller, triggering a real time counting of the protocol time interval, whose beginning and end information is presented on the display (43) and transmitted to the computer application by wireless communication.

Constant Force Actuator Construction

For a better understanding of the invention some examples are given which represent preferential embodiments of the invention but are not meant to limit the scope of this invention.

Figure 1A:
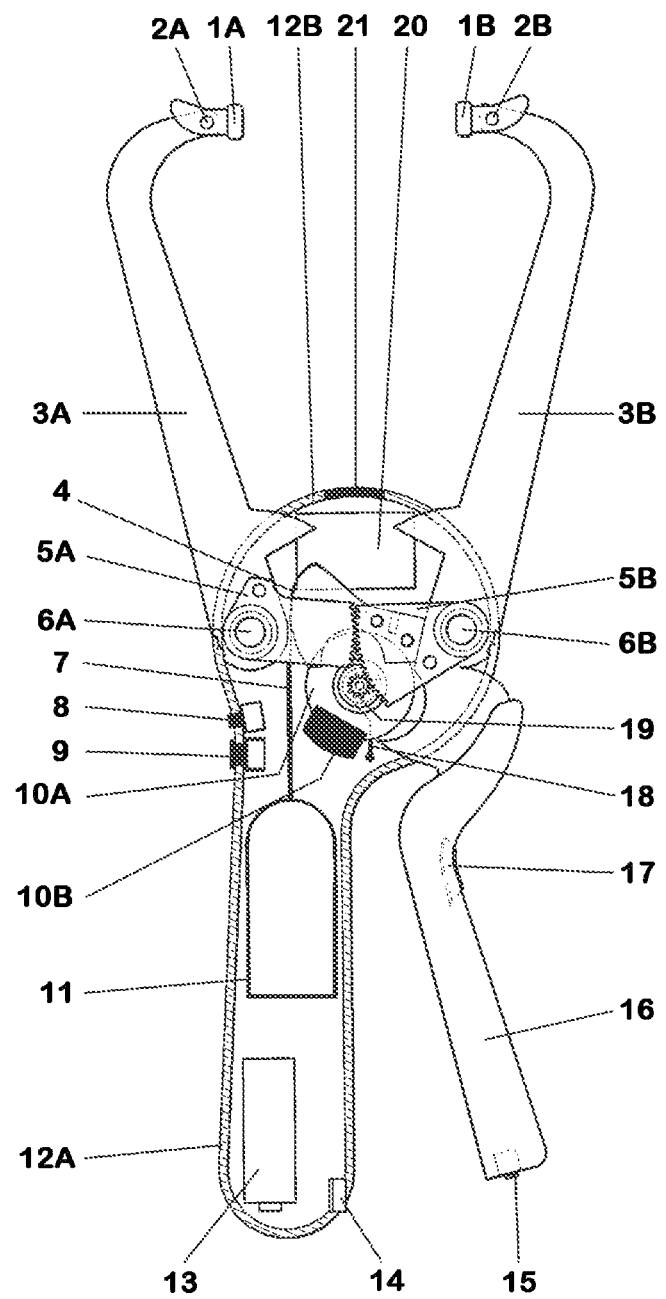
FIGS. 1A and 1B: Representation of the device.
1A and 1B—End tip A and B, respectively;
2A and 2B—Axis of rotation of the end tip A and B, respectively;
3A and 3B—Jaw A and B, respectively;
4—Force compensation cam;
5A and 5B—Mechanical transmission elements A and B, respectively.
Figure 1B:
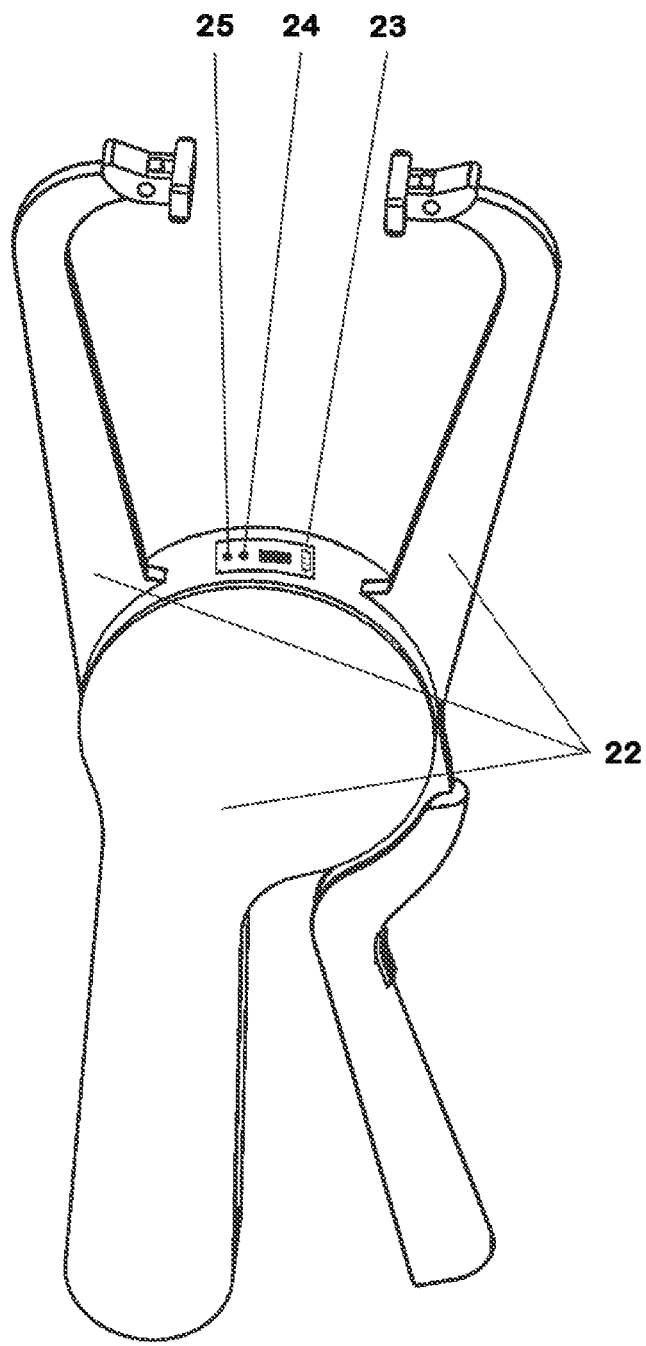
Figure 2:
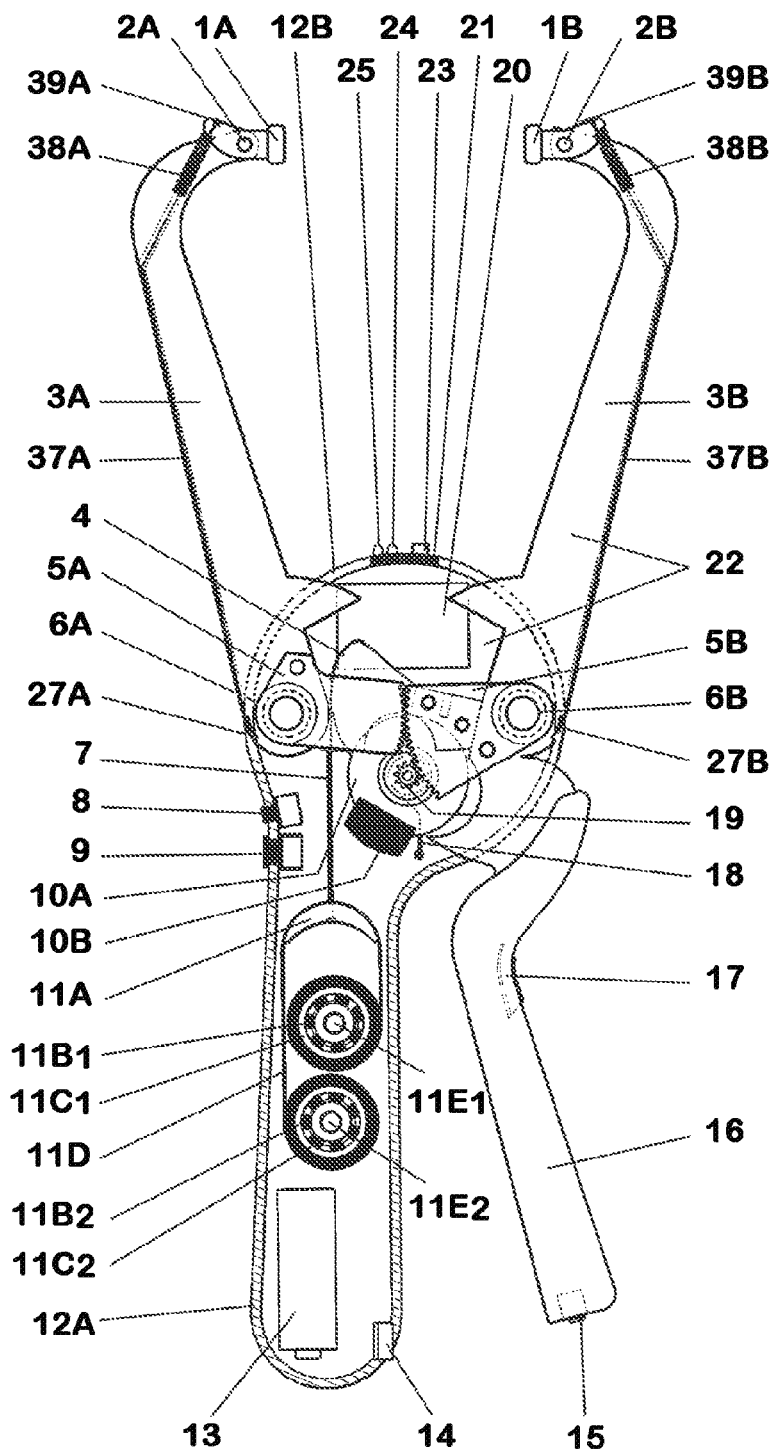
FIG. 2: Representation of the device internal constitution.
1A and 1B—End tip A and B, respectively;
2A and 2B—Axis of rotation of end tip A and B, respectively;
3A and 3B—Jaw A and B, respectively;
4—Force compensation cam;
5A and 5B—Mechanical transmission element A and B, respectively;
6A and 6B—Axis of rotation of jaw A and B, respectively;
7—Inextensible cable;
8—On/off switch;
9—Device for remote interaction;
10A—Encoded sensing element;
10B—Reading sensing element;
11A—Crescent shaped saddle;
11B1 and 11B2—Bearing for support of winding drum (11C1 and 11C2), respectively;
11C1 and 11C2—Winding drum for the ends of the elastic element of constant force (11D);
11D—Elastic element of constant force;
11E1 and 11E2—Axis of rotation of the bearing (11B1 and 11B2), respectively;
12A—Device handle;
12B—Device cylindrical body;
13—Power supply;
14—Power charging jack;
15—Measurement reset button;
16—Lever;
17—Trigger button for the time interval of the measurement protocol;
18—Spiral spring of the encoded sensing element;
19—Mechanical element for increasing measurement resolution;
20—Electronic system;
21—Window for communication and visualization of the light indicators;
22—Device lateral faces;
23—Light indicator of the device power supply status;
24—Light indicator of the on/off status of the electronic system (20);
25—Light indicator of the on/off status of the device connection to the remote station;
27A and 27B—Fixed axis of rotation of the bars (26A and 26B), respectively;
37A and 37B—Inextensible cable located in jaw (3A and 3B), respectively;
38A and 38B—Elastic element located in jaw (3A and 3B), respectively;
39A and 39B—Anchoring point of the inextensible cable (37A and 37B) on the end tip (1A and 1B), respectively.
Figure 3:
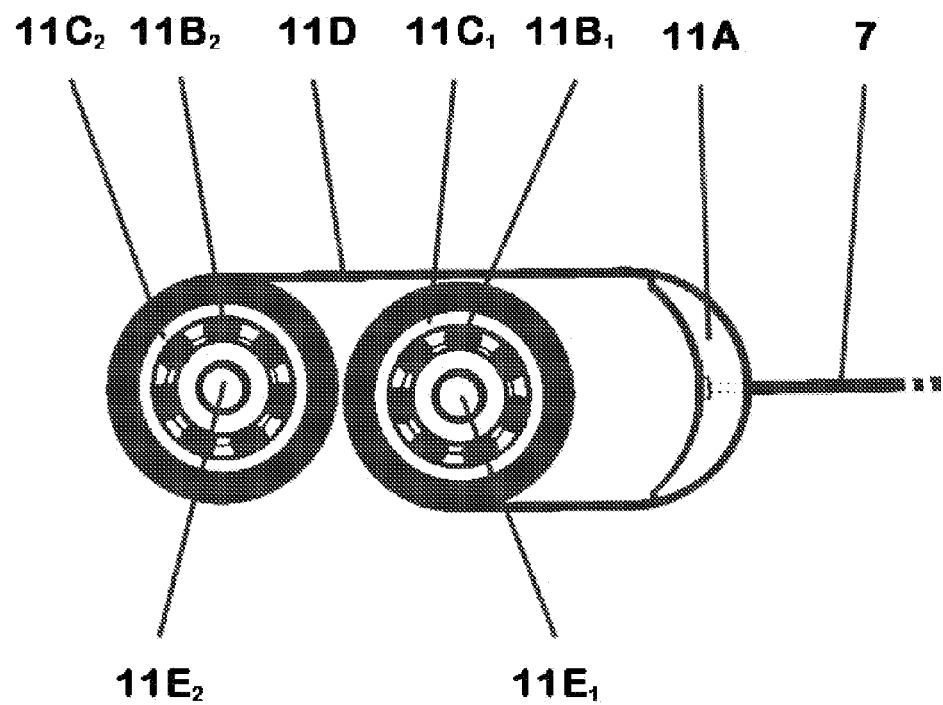
FIG. 3: Representation of a mechanism called constant force actuator (11), with the following components:
7—Inextensible cable;
11A—Crescent shaped saddle;
11B1 and 11B2—Bearing for support of winding drum (11C1 and 11C2), respectively;
11C1 and 11C2—Winding drum for the ends of the elastic element of constant force (11D);
11D—Elastic element of constant force;
11E1 and 11E2—Axis of rotation of the bearing (11B1 and 11B2), respectively.

Example 1 referring to FIG. 3: this constant force actuator mechanism is located in the device handle (12A) and comprises one crescent shaped saddle (11A), two drums (11C1) and (11C2), two bearings (11B1) and (11B2), two rotation axes (11E1) and (11E2) and one constant force spring (11D).

The constant force actuator (11) is based on a constant force spring (11D). It doubles the force of the spring (11D) by coiling both its ends over drums (11C1) and (11C2), supported by bearings (11B1) and (11B2) whose inner races are connected to the axes of rotation (11E1) and (11E2), respectively. The natural tendency of the spring is to wrap around the drums (11C1) and (11C2) thus exerting a tensile force at the end of the coupling. This force is conveyed to the transmission chain through a crescent shaped saddle (11A) on which rests the elastic element of constant force (11D), the saddle being pulled by the inextensible cable (7).

The use of two overlapping springs of constant force (11D), i.e., the placement of two overlapping constant force springs, enables the doubling of the strength of the constant force actuator. In case a greater tensile force is needed, the number of overlapping springs can be augmented in order to increase the force/size ratio.

Forms of the Mechanism for Parallel Displacement of the End Tips

Figure 4:
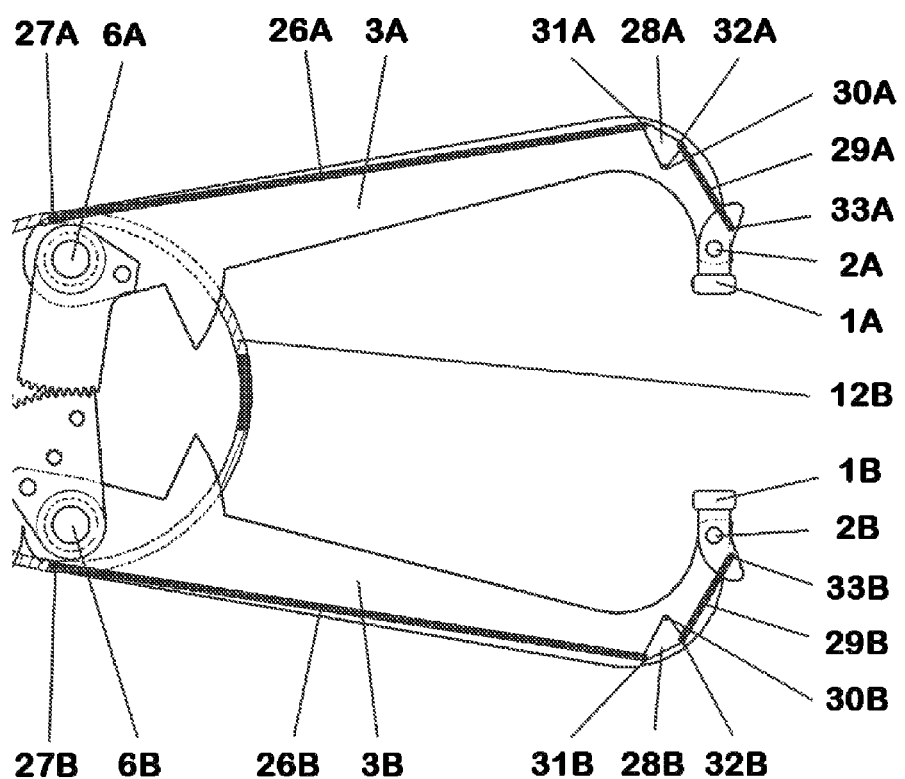
FIG. 4: Representation of a transmission mechanism of angular movement to the end tips, for maintaining the parallelism of their clamping faces, using a parallelogram based configuration with bars in compression, with the following components:
1A and 1B—End tip A and B, respectively;
2A and 2B—Axis of rotation of the end tip A and B, respectively;
3A and 3B—Jaw A and B, respectively;
6A and 6B—Axis of rotation of the jaw A and B, respectively;
12B—Device cylindrical body;
26A and 26B—Primary parallelogram bar A and B, respectively;
27A and 27B—Fixed axis of rotation of the bars (26A and 26B), respectively;
28A and 28B—Coupling element located in jaw (3A and 3B), respectively;
29A and 29B—Secondary parallelogram bar A and B, respectively;
30A and 30B—Fixed axis of rotation of the coupling element (28A and 28B), respectively;
31A and 31B—Floating hinge of the primary bar (26A and 26B) in the coupling element (28A and 28B), respectively;
32A and 32B—Floating hinge of the secondary bar (29A and 29B) in the coupling element (28A and 28B), respectively;
33A and 33B—Floating hinge of the secondary bar (29A and 29B) in the end tip (1A and 1B), respectively.

Example 2 referring to FIG. 4: this mechanism is present in both jaws and equally applied. It consists of a primary parallelogram and a secondary parallelogram.

The primary parallelogram consists of two pairs of parallel line segments: the first pair is formed by the line segment between the axes of rotation (27A) and (31A) and the line segment between the axes of rotation (6A) and (30A); the second pair is formed by the line segment between the axes of rotation (27A) and (6A) and the line segment between the axes of rotation (31A) and (30A).

The secondary parallelogram is composed by two pairs of parallel line segments: the first is formed by the line segment between the axes of rotation (32A) and (33A) and the line segment between the axes of rotation (30A) and (2A); the second is formed by the line segment between the axes of rotation (32A) and (30A) and the line segment between the axes of rotation (33A) and (2A).

These parallelograms are interconnected by the coupling element (28A) that rotates around the axis of rotation (30A) in conjunction with the jaw (3A).

In the parallelograms listed above, the axes (27A) and (6A) are fixed to the device body, the axes (30A) and (2A) are fixed to the jaw (3A), while the remaining axes (31A), (32A) and (33A) are floating and can move relative to the device housing (12B) and the jaw (3A).

The mechanism installed in the jaw (3B) is identical to that described previously, changing the reference from A to B, with the exception of that of the device housing (12B).

During the movement of the jaw (3A) and due to the fact that the sides of the parallelograms are materialized by rigid bars (26A) and (29A), the side of the primary parallelogram between the axes (27A) and (6A) remains stationary in relation to device housing (12B). This implies that the primary parallelogram side between the axes (30A) and (31A) is forced to remain parallel to the line segment between the axes (27A) and (6A), following the movement of the jaw (3A). Since the secondary parallelogram side between the axes (30A) and (32A) is defined in the coupling element (28A), on which is also defined the side of the primary parallelogram between the axes (30A) and (31A), the relative position of these two segments remains unchanged throughout the movement of the jaw (3A). Thus, the secondary parallelogram side between the axes (2a) and (33A) is forced to maintain its angular position relative to the side between the axes (27A) and (6A) of the primary parallelogram. The end tip face (1A) and the secondary parallelogram side between the axes of rotation (2A) and (33A) are defined in the same part, the end tip (1A), forcing the end tip face to keep its angular position in relation to the device housing (12B). For the mechanism located on the jaw (3B) its operation is analogous to that just described for the jaw (3A).

As a result of this operation, the faces of the end tips (1A) and (1B) remain parallel to each other during the movement of the jaws (3A and 3B), and only have translation movement relative to the body of the device.

Figure 5:
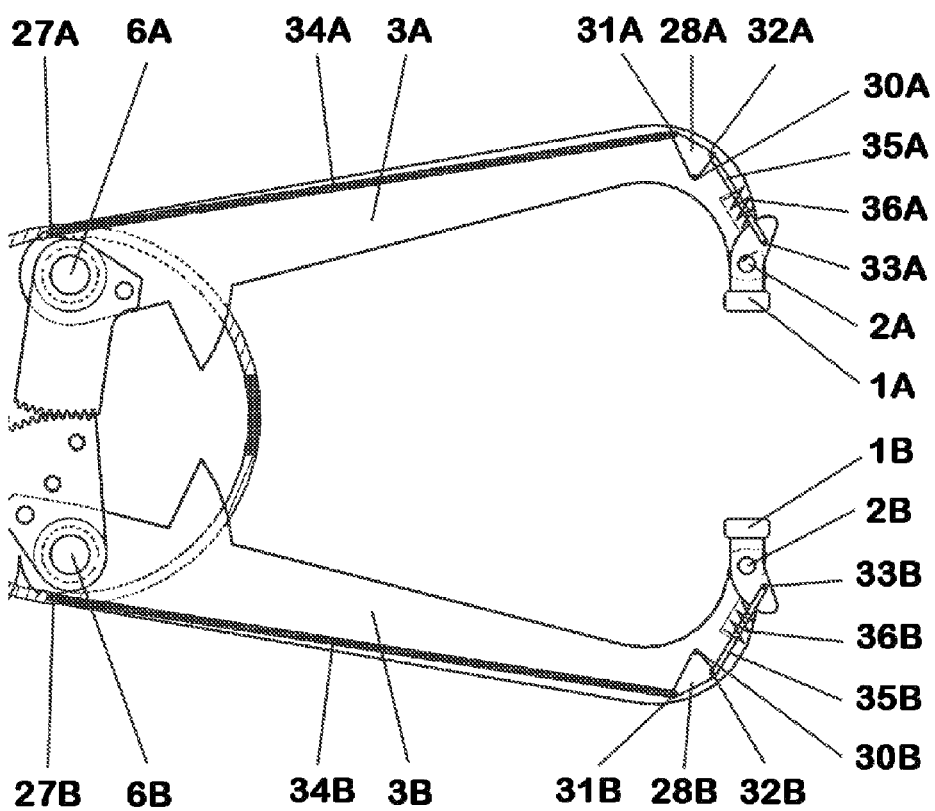
FIG. 5: Representation of a transmission mechanism of angular movement to the end tips, for maintaining the parallelism of their clamping faces, using a parallelogram based configuration with bars in tension and/or compression, with the following components:
1A and 1B—End tip A and B, respectively;
2A and 2B—Axis of rotation of end tip A and B, respectively;
3A and 3B—Jaw A and B, respectively;
6A and 6B—Axis of rotation of jaw A and B, respectively;
27A and 27B—Fixed axis of rotation of the inextensible cable/bar (34A and 34B), respectively;
28A and 28B—Coupling element located in jaw (3A and 3B), respectively;
30A and 30B—Fixed axis of rotation of the coupling element (28A and 28B), respectively;
31A and 31B—Floating hinge of the inextensible cable/primary bar (34A and 34B) in the coupling element (28A and 28B), respectively.

Example 3 referring to FIG. 5: the description of the mechanism pertaining to this example is similar to that of the mechanism of example 2. The replacement of the elements (26A) and (29A) by inextensible cables (34A) and (35A) requires the introduction of an elastic element (36A) for keeping these two inextensible cables always in tension whatever the opening of the jaws (3A and 3B).

Thus, the conclusion of example 2 still holds regarding the end tip faces (1A and 1B) remaining parallel during the movement of the jaws (3A and 3B).

The mechanism installed in the jaw (3B) is identical to that described previously, changing the reference from A to B.

It should be noted that either one of the inextensible cables (34A) and (35A) located in each of the jaws (3A) and (3B), can be replaced by a rigid bar.

Example 4 referring to FIG. 6: the length of the path between the anchoring points (27A) and (39A), established by the inextensible cable (37A) pulled tight by the action of the elastic element (38A), will remain constant whatever the jaw (3A) angle. Due to the equal length of the line segment between the axis (6A) and the anchoring point (27A) and the one between the axis (2A) and the anchoring point (39A) and given that the anchoring point (27A) is fixed to the device housing (12B), the faces of the end tips (1A) and (1B) remain parallel to each other during the movement of the jaws (3A and 3B), and only have translation movement relative to the device housing.

The mechanism installed in the jaw (3B) is identical to that described previously, changing the reference from A to B, with the exception of that of the device housing (12B).

Example 5 referring to FIG. 7: the length of the path e between the anchoring points (27A) and (39A) established through a flexible element (40A) confined in its housing (41A), remains constant whatever the jaw (3A) angle. The flexible element (40A) works in compression and is confined in its housing (41A) in jaw (3A), with sliding clearance. Due to the equal length of the line segment between the axis (6A) and the anchoring point (27A) and the one between the axis (2A) and the anchoring point (39A) and given that the anchoring point (27A) is fixed to the device housing (12B), the faces of the end tips (1A) and (1B) remain parallel to each other during the movement of the jaws (3A and 3B), and only have translation movement relative to the device housing.

The mechanism installed in the jaw (3B) is identical to that described previously, changing the reference from A to B, with the exception of that of the device housing (12B).

Implementations of Navigation Methods in the Graphical Interface of the Software Application Example 6 referring to FIG. 8: the joystick-type navigation button (9A) triggers five distinct command actions on the software application cursor, allowing the operator to navigate the graphical interface. There are four steering actions and the fifth is for selection confirmation.

Example 7 referring to FIG. 9: the touchscreen (9B) triggers directional movements of the software application cursor, as a result of operator sliding actions on its surface. The confirmation of the selection is achieved by a touch on the touchscreen.

Implementations of the Mechanism for Simultaneous Opening of the Jaws

Example 8 referring to FIG. 11: the mechanism for simultaneous opening of the jaws (3A and 3B) is located inside the device housing (12B) and comprises two toothed sectors (44A and 44B) with equal pitch circle attached to the jaws (3A and 3B) and with rotation axes (6A and 6B), respectively. The rotation imposed on the sector (44B) by the action of the lever (16), transmits the motion to the toothed sector (44A) leading to the simultaneous opening of the two jaws (3A and 3B) and with equal amplitude.

Example 9 referring to FIG. 12: this mechanism for simultaneous opening of the jaws (3A and 3B) is located inside the device housing (12B) and consists of a hinged four-bar mechanism embodied by: a line segment between the axes (6A) and (47), a line segment between the axes (6B) and (46), a transmission bar (45) articulated between the axes (46) and (47) attached to the jaws (3A and 3B) and a bar materialized by the device housing (12B) between the axes (6A) and (6B).

The rotation of the lever (16) leads to the rotation of the segment between the axes (46) and (6B) around the axis (6B), which in turn forces the displacement of the transmission bar (45), causing the rotation of the segment lying between the axes (47) and (6A) around the axis (6A) and the consequent rotation of the jaw (3A) with an amplitude equal to that of the jaw (3B). These rotations have the same amplitude since the line segments included between the pairs of axes (6A and 47) and (6B and 46) are of equal length.

The following claims additionally represent preferential embodiments of the present invention.

The invention claimed is:

1. A device for measuring the thickness of skin folds that comprises:
    a device housing (12B) with an extension for handling (12A);
    a structure with two jaws (3A and 3B) with hinged end tips (1A and 1B) mechanically oriented and one lever (16)
    a constant force actuator mechanism (11); and
    a cam (4) with a profile that compensates the variation of a force arm length in the jaws (3A and 3B) and which provides the transmission of the force generated by the said constant force actuator (11),
    wherein said constant force actuator mechanism (11) includes:
    one crescent shaped saddle (11A) which supports at least one constant force elastic element (11D), two drums (11C1, 11C2), two bearings (11B1, 11B2), two rotation axes (11E1, 11E2).

2. A device for measuring the thickness of skin folds according to claim 1, wherein the jaws (3A and 3B) are hinged on two rotation axes (6A and 6B) whose centre distance is large enough to correspond to one half of the maximum opening of the jaws (3A and 3B).

3. A device for measuring the thickness of skin folds according to claim 1, wherein the end tips (1A and 1B) are hinged and mechanically oriented to keep the parallelism between their contact faces through a mechanism actuated by the opening/closing of the jaws (3A and 3B).

4. A device for measuring the thickness of skin folds according to claim 1 further comprising a movement transmission mechanism to the end tips (1A and 1B) utilizing the following guidance systems: one mechanism of parallelograms configuration with tensile and/or compression bars; one inextensible cable mechanism under tension by elastic element action; one flexible element mechanism confined in its housing.

5. A device for measuring the thickness of skin folds according to claim 1, wherein the elastic constant force element (11D) is a spring.

6. A device for measuring the thickness of skin folds according to claim 1 further comprising a mechanism for multiplying the angular displacement of the jaws (3A and 3B) that increases the resolution of the measurement of the distance between the faces of the end tips (1A and 1B).

7. A device for measuring the thickness of skin folds according to claim 1, wherein the housing (12A and 12B) accommodates all the mechanical elements for force transmission of the constant force actuator (11) to the jaws (3A and 3B), a sensing element (10A and 10B) and an electronic system (20).

8. A device for measuring the thickness of skin folds according to claim 1, further comprising an electronic system (20) consisting of one rechargeable power supply system, one signal conditioning system, one dedicated microcontroller and one system for wireless communication.

9. A device for measuring the thickness of skin folds according to claim 1, further comprising a window (21) that allows wireless communication with a remote station (42) and the visualization of a light indicator for user information.

10. A device for measuring the thickness of skin folds according to claim 1, further comprising one on/off switch, one display, one navigation system in the device symmetry plan, in order to make the handling of the device independent of the dominant hand of the operator.

11. A device for measuring the thickness of skin folds according to claim 2, wherein the end tips (1A and 1B) are hinged and mechanically oriented to keep the parallelism between their contact faces through a mechanism actuated by the opening/closing of the jaws (3A and 3B).

* * * * *